United States Patent [19]

Storz

[11] Patent Number: 5,677,179
[45] Date of Patent: *Oct. 14, 1997

[54] ISOLATION AND DIAGNOSIS OF CORONAVIRUSES AS A FACTOR IN BOVINE SHIPPING FEVER, AND A CELL LINE FOR CULTURING BOTH THOSE AND OTHER BOVINE CORONAVIRUSES

[75] Inventor: Johannes Storz, Baton Rouge, La.

[73] Assignee: Board of Supervisors of Louisiana State University and Agricultural and Mechanical College, Baton Rouge, La.

[*] Notice: The portion of the term of this patent subsequent to Jun. 15, 2014, has been disclaimed.

[21] Appl. No.: 756,791

[22] Filed: Nov. 26, 1996

Related U.S. Application Data

[63] Continuation of Ser. No. 260,089, Jun. 15, 1994, Pat. No. 5,580,778.

[51] Int. Cl.$^6$ .................... C12N 5/06; C12N 1/00; C12N 1/04; C12Q 1/70
[52] U.S. Cl. .................... 435/325; 435/5; 435/243; 435/260; 435/366; 435/948
[58] Field of Search .................... 435/5, 325, 243, 435/260, 948, 366

[56] References Cited

U.S. PATENT DOCUMENTS 5,580,778  12/1996  Storz .................... 435/240.2

OTHER PUBLICATIONS

Benfield et al. J. Clin. Microbiol. 28 (6) 1454–1457 "Cell Cutive Propagation of a Carbonavirus . . . " 1990.
Storz et al. "Enhancement of Player Formation . . . " Infect Immun. 31(3) 1214–1222 1981.
St Cyr–Coats et al. J Vet Med B 35 48–56 "Bovine Caronvirus –Induct Cytopathic Expression . . . " 1988.
Jiménez et al "Isolieung von Coronauren . . . " Thomelatin J Vet Med B 36 635–638 1989.
J. Moreno–López, "Acute Respiratory Disease in Cattle," in Z. Dinter et al. (eds.), *Virus Infections of Ruminants*, pp. 551–554 (1990).
O. Straub, "Infectious Bovine Rhinotracheitis," in Z. Dinter et al. (eds), *Virus Infections of Ruminants*, pp. 71–108 (1990).
B. Liess, "Bovine Viral Diarrhea Virus," in Z. Dinter et al. (eds.), *Virus Infections of Ruminants*, pp. 247–266 (1990).
"Coronaviridae," in Z. Dinter et al. (eds.), *Virus Infections of Ruminants*, p. 295 (1990).
C. Mebus, "Neonatal Calf Diarrhea Virus," in Z. Dinter et al., (eds.), *Virus Infections of Ruminants*, pp. 297–300 (1990).
J. Espinasse, "Winter Dysentery of Adult Cattle Virus," in Z. Dinter et al. (eds.), *Virus Infections of Ruminants*, pp. 301–307 (1990).

D. Bryson, "Parainfluenza–3 Virus in Cattle," in Z. Dinter et al. (eds.), *Virus Infections of Ruminants*, pp. 319–333 (1990).
G. Wellemans, "Bovine Respiratory Syncytial Virus," in Z. Dinter et al. (eds), *Virus Infections of Ruminants*, pp. 363–375 (1990).
M. McNulty et al., "Coronovirus Infection of the Bovine Respiratory Tract," Vet. Micro., vol. 9, pp. 425–434 (1984).
D. Reynolds et al., "Studies on the Relationship between Coronaviruses from the Intestinal and Respiratory Tracts of Calves," Arch. Virol., vol. 85, pp. 71–83 (1985).
K. St. Cyr–Coats et al., "Bovine Coronavirus–Induced Cytopathic Expression and Plaque Formation: Host Cell and Virus Strain Determine Trypsin Dependence," J. Vet. Med. B, vol. 35, pp. 48–56 (1988).
W. Tompkins et al., "Culture and Antigenic Properties of Newly Established Cell Strains Derived from Adenocarcinomas of the Human Colon and Rectum," J. Natl. Canc. Inst., vol. 52, pp. 1101–1106 (1974).
R. Heckert et al., "A Longitudinal Study of Bovine Coronavirus Enteric and Respiratory Infections in Dairy Calves in Two Herds in Ohio," Vet. Micro., vol. 22, pp. 187–201 (1990).
C. Jiménez et al., "Isolierung von Coronaviren in der Zellkultur aus Nasentupferproben atemwegskranker Kälber in der Bundesrepublik Deutschland," J. Vet. Med. B, vol. 36, pp. 635–638 (1989) (English translation provided.).
K. Möstl et al., "Ursächliche Beteiligung boviner Coronaviruen an respiratorischen Krankheitsausbrüchen bei Kälbern und pathogenetisch–immunologische Überlegungen hierzu," Dtsch. tierärztl. Wschr., vol. 95, pp. 19–22 (1988) (English translation provided.).
W. Herbst et al., "Serologisch–diagnoistiche Untersuchungen zum Vorkommen von Coronavirusinfektionen bei Atemwegserkrankungen des Rindes," Berl. Münch. Tierärztl. Wschr., vol. 102, pp. 129–131 (1989) (English translation provided.).
K. St. Cyr–Coats et al., "Structural Proteins of Bovine Coronavirus Strain L9: Effects of the Host Cell and Trypsin Treatment," Arch. Virol., vol. 103, pp. 35–45 (1988).
Benefield et al., "Cell Culture Propagation of a Coronavirus Isolated from Cows With Winter Dysentery," J. Clin. Microbiol. 28(6) 1454–1457 (1990).
Storz et al., "Enhancement of Plaque Formation and Cell Fusion of an Enteropathogenic Coronavirus by Trypsin Treatment," Infect. Immun. 31(3) 1214–1222 (1981).

*Primary Examiner*—Nancy Degen
*Attorney, Agent, or Firm*—John H. Runnels

[57] ABSTRACT

Coronaviruses can be a significant factor in bovine shipping fever. A new human rectal tumor cell line, HRT-18G, is suitable as a host cell line for the propagation of these bovine respiratory coronavirus-shipping fever viruses, and also is well suited for the propagation of other bovine coronaviruses.

10 Claims, No Drawings

ISOLATION AND DIAGNOSIS OF CORONAVIRUSES AS A FACTOR IN BOVINE SHIPPING FEVER, AND A CELL LINE FOR CULTURING BOTH THOSE AND OTHER BOVINE CORONAVIRUSES

This is a continuation of application Ser. No. 08/260,089, filed Jun. 15, 1994, now U.S. Pat. No. 5,580,778, the entire disclosure of which is incorporated by reference.

This invention pertains to the isolation and diagnosis of coronaviruses as a factor in bovine shipping fever, and to a cell line suited for culturing both those and other coronaviruses.

Bovine respiratory and enteric diseases are the most costly diseases in animal agriculture. "Shipping fever" is one of the most common, serious, and costly diseases affecting feedlot cattle. The symptoms of shipping fever include fever, nasal discharge, and respiratory disease that includes pneumonia-like symptoms. Shipping fever can cause death of the animal, in which case fibrinous pneumonia is typically observed on necropsy.

Shipping fever has generally been associated with a combination of stress and mixed viral and bacterial infections. A virus is usually the primary pathogen, and secondary bacterial infections can also develop. The first such synergism demonstrated for shipping fever was that between a bovine parainfluenza-3 ("PI3") virus and Pasteurella infections. Other viruses that have been associated with shipping fever include bovine viral diarrhea virus ("BVDV"), bovine respiratory syncytial virus ("BRSV"), and infectious bovine rhinotracheitis virus ("IBRV").

For general background, see also O. Straub, "Infectious Bovine Rhinotracheitis," in Z. Dinter et al. (eds.), *Virus Infections of Ruminants*, pp. 71–108 (1990); B. Liess, "Bovine Viral Diarrhea Virus," in Z. Dinter et al. (eds.), *Virus Infections of Ruminants*, pp. 247–266 (1990); "Coronaviridae," in Z. Dinter et al. (eds.), *Virus Infections of Ruminants*, p. 295 (1990 ); C. Mebus, "Neonatal Calf Diarrhea Virus," in Z. Dinter et al. (eds.), *Virus Infections of Ruminants*, pp. 297–300 (1990); J. Espinasse, "Winter Dysentery of Adult Cattle Virus," in Z. Dinter et al. (eds.), *Virus Infections of Ruminants*, pp. 301–307 (1990); D. Bryson, "Parainfluenza-3 Virus in Cattle," in Z. Dinter et al. (eds.), *Virus Infections in Ruminants*, pp. 319–333 (1990); and G. Wellemans, "Bovine Respiratory Syncytial Virus," in Z. Dinter et al. (eds.), *Virus Infections of Ruminants*, pp. 363–375 (1990).

Although a number of viral pathogens have been implicated in shipping fever, vaccination of cattle against the known viral pathogens has not eliminated the disease. Thus there remains an unfilled need for a method to diagnose other, previously unknown viral factors in shipping fever.

Coronaviruses are a family of viruses that have been implicated in other diseases in both humans and animals. Coronaviruses possess a single, positive-stranded RNA genome of about 31 kb. The name "corona" is given to this viral family because of protein spikes on the viral envelope that give the appearance of a corona-like ring under an electron microscope.

A type called bovine enteric coronaviruses ("BECV's") have previously been known to be etiological factors in bovine enteric disease (including enteric-respiratory diseases in which respiratory symptoms appear in addition to diarrhea), especially in newborn calves. However, coronaviruses have not previously been identified as a viral factor in shipping fever. In fact, coronaviruses have been infrequently implicated in other bovine disease processes. See J. Moreno-López, "Acute Respiratory Disease in Cattle," in Z. Dinter et al. (eds.), *Virus Infections of Ruminants*, pp. 551–54 (1990).

Coronaviruses were first isolated in the 1970's from neonatal calves with signs of diarrhea. These cytopathogenic BECV's have been established as a causal agent of enteric disease during calfhood. BECV's may also be an agent for winter dysentery in adult cattle. It has been observed that coronaviruses have been shed from the respiratory tract of calves with enteric disease.

Bovine coronaviruses ("BCV's") have previously been quite difficult for workers to isolate and propagate. A few strains of BECV have been isolated and propagated in bovine embryonic kidney cells, bovine embryonic lung cells, bovine organ cultures from fetal trachea and intestine, and a line of human rectal tumor cells known as "HRT-18." An HRT-18 cell line is susceptible, albeit minimally susceptible, to a number of coronaviruses from animals. The HRT-18 cell line has allowed replication of various strains of BECV's. However, commonly available HRT-18 cell lines have properties making them less than ideal for the propagation of some coronaviruses. HRT-18 cell lines are heterogeneous populations of cells having different growth characteristics, sizes and shapes. HRT-18 cells also have variable susceptibility to bovine coronaviruses; some HRT-18 cells are susceptible to the viruses, while others are only minimally susceptible. Trypsin in the growth medium is needed for BECV's to exhibit cytopathic expression in HRT-18 cells. There remains a unfilled need for cell lines that are better suited for the in vitro propagation of bovine coronaviruses.

M. McNulty et al., "Coronavirus Infection of the Bovine Respiratory Tract," Vet. Micro., vol. 9, pp. 425–34 (1984) reported the isolation of coronavirus from calves having respiratory symptoms on a tracheal-organ culture. This virus was then used to inoculate 10- to 14-day-old calves, who then developed first a cough and nasal discharge, and later developed diarrhea.

D. Reynolds et al., "Studies on the Relationship between Coronaviruses from the Intestinal and Respiratory Tracts of Calves," Arch. Virol., vol. 85, pp. 71–83 (1985) reported the detection of coronaviruses by an immunofluorescence test from both respiratory and enteric tissue of calves with diarrhea. Coronaviruses were cultured in HRT-18 cells. The absence of any sign of coronavirus in the lower respiratory tract and of any symptoms of respiratory disease led the authors to conclude that coronaviruses should not be considered a factor in calf pneumonia.

K. St. Cyr-Coats et al., "Bovine Coronavirus-Induced Cytopathic Expression and Plaque Formation: Host Cell and Virus Strain Determine Trypsin Dependence," J. Vet. Med. B, vol. 35, pp. 48–56 (1988) discloses the propagation of bovine coronaviruses obtained from diarrheal samples in HRT-18 cells.

W. Tompkins et al., "Cultural and Antigenic Properties of Newly Established Cell Strains Derived from Adenocarcinomas of the Human Colon and Rectum," J. Natl. Canc. Inst., vol. 52, pp. 1101–1106 (1974) discloses the original establishment of human rectal tumor cell line HRT-18.

R. Heckert et al., "A Longitudinal Study of Bovine Coronavirus Enteric and Respiratory Infections in Dairy Calves in Two Herds in Ohio," Vet. Micro., vol. 22, pp. 187–201 (1996) reported the use of immunofluorescence and ELISA to study the presence of coronaviruses in the respiratory tract and in the intestine of calves up to 4 months of age. BECV infections were reported to be common, and were usually associated with enteric disease. Only mild respiratory disease symptoms were associated with the presence of BECV in the respiratory tract.

C. Jiménez et al., "Isolierung von Coronaviren in der Zellkultur aus Nasentupferproben atemwegskranker Kälber in der Bundesrepublik Deutschland," J. Vet. Med. B, vol. 36, pp. 635–638 (1989) reported the isolation of coronaviruses from the respiratory tract of four young calves by culturing in HRT-18 cells. The young calves, ages 3 to 16 weeks, had symptoms of respiratory disease, including fever, as well as symptoms of enteric disease. However coronaviruses could not be isolated from nasal-swab samples taken from eleven other calves with similar clinical symptoms.

K. Möstl et al., "Ursächliche Beteiligung boviner Coronaviren an respiratorischen Krankheitsausbrüchen bei Kälbern und pathogenetisch-immunologische Überlegungen hierzu." Dtsch. tierärztl. Wschr., vol. 95, pp. 19–22 (1988) reported the detection of coronaviral antigen from nasal swabs of young Austrian calves (from one herd) with respiratory disease by hemagglutination of rat erythrocytes (red blood cells). An immunofluorescence test was also reported to detect antibodies to enteric BECV antigen. Samples were taken from two groups of cattle, one aged two to four months and the other aged five to thirteen months. The younger cattle had no fever, but did display nasal discharge and cough. The older cattle displayed greater respiratory disease signs, including feverish pneumonia. Only one animal had signs of diarrhea. Possible co-factors in respiratory coronavirus infections in the calf were discussed—co-factors such as relocation or co-infections.

W. Herbst et al., "Serologisch-diagnostiche Untersuchungen zum Vorkommen von Coronavirusinfektionen bei Atemwegserkrankungen des Rindes," Berl. Münch. Tierärztl. Wschr., vol. 102, pp. 129–131 (1989) reported the detection of coronavirus antibodies with BECV antigen in a hemagglutination inhibition test in calves from thirty seven herds with symptoms of respiratory disease. Coronaviruses were said to be implicated in respiratory disease.

It has been unexpectedly discovered that coronaviruses are emerging as a substantial factor in causing shipping fever. The present invention provides a method to diagnose this previously unappreciated causal factor in shipping fever.

A novel human rectal tumor cell line, identified as "HRT-18G," has been cultured. The novel HRT-18G cell line is a suitable host for bovine shipping fever coronaviruses. The HRT-18G cell line also has properties making it an improved host cell line for the propagation of other bovine coronaviruses generally, including BECV's.

In the fall of 1993, symptoms of shipping fever were observed at a high rate in feedlot cattle shipped from six different midwestern and western states. These cattle did not have symptoms of enteric disease. Using the techniques of the present invention, thirty-eight coronaviral strains with unique properties were isolated from nasal samples taken from these cattle. This surprising finding indicated that coronaviruses are emerging as a new factor in shipping fever. This new viral factor was not detected by diagnostic approaches conventionally used for shipping fever. The novel HRT-18G cell line played a cardinal role in the isolation of these newly recognized coronaviruses.

It is possible that coronaviruses as a factor in shipping fever were simply overlooked in past investigations. However, it is believed that a more likely hypothesis is that these coronaviruses represent an emerging viral factor in a cattle population already effectively vaccinated against other known viral infections, such as PI3.

The HRT18G Cell Line

Novel cell line HRT-18G was derived from an HRT-18 cell line. The HRT-18G cells maintain the properties of specialized epithelial cells (such as microvilli, a polarized structure, and desmosomes).

The HRT-18G cell line was derived from the "parent" HRT-18 cell line by successive culture of cells in different media. The HRT-18G cells were uniquely susceptible to the newly recognized class of bovine respiratory coronaviruses (BRCV's) that were isolated from nasal samples of cattle affected with shipping fever. It was observed that the HRT-18G cells grew optimally when the growth medium was prepared from ultra-pure water instead of ordinary distilled water.

HRT-18G cells were propagated by seeding 5 ml of a $2 \times 10^5$ cells/ml suspension of cells into a 25 cm$^2$ tissue culture flask, and incubating at 37° C. under 5% $CO_2$. The growth medium comprised Dulbecco's modified minimum essential medium (DMEM), with 44 μM sodium bicarbonate buffer. The medium was prepared with highly pure water that had been doubly deionized, and then filter sterilized. Penicillin (100 units/ml) and streptomycin (100 μg/ml) were added to the medium. The medium was supplemented with 5% heat-inactivated bovine fetal serum that was free of antibodies against known bovine viruses (including known bovine coronaviruses).

HRT-18G cells cultured in the above medium formed a confluent, uniformly clean monolayer following two to three days incubation at 37° C. The cells were small and uniform in size when observed under native conditions with either an inverted-phase contrast microscope, or an ordinary light microscope. The cells formed a smooth, dense, single-layered, uniform cell lawn.

By contrast, a culture of the "parent" HRT-18 cells contains cells of differing sizes, and forms patches of multicell layers. Without wishing to be bound by this theory, it is believed that there are populations of different cell types in the parent HRT-18 cell line, resulting in the formation of swirls and cell conglomerates containing some foci of higher cell density and smaller cells, and other foci of lower cell density and large, polymorphic cells.

Completely monolayered HR-18G cultures were subpassaged for cell propagation, and for producing cell cultures for bovine. coronavirus propagation or plaque titration. Cell cultures were washed with Dulbecco's phosphate-buffered saline (DPBS) to remove traces of the previous growth medium. The cell cultures were then treated with a 0.5% trypsin solution in DPBS, without magnesium or other divalent cations. The trypsin-treated cell cultures were then incubated at 37° C. for a few minutes under intermittent observation to detect detachment of single cells. After the cells had detached from the substrate and from one another, they were counted and suspended in an appropriate volume of growth medium. Samples were stained with a 0.5% trypan blue solution, so that viable, unstained cells could be counted in a hemocytometer. Cells were then suspended in the appropriate volume of growth medium at a density of $2 \times 10^5$ cells/ml, and seeded into culture flasks or Petri dishes for propagation.

To preserve HRT-18G cells in the frozen state, the cells were first suspended at a concentration of $2 \times 10^6$ cells/ml in DMEM, fortified with 10% heat-inactivated bovine fetal serum and 10% dimethylsulfoxide ("DMSO"). The suspensions were distributed in 1.0 ml volumes into cryovials, which were then sealed. These vials were placed into a controlled rate cell freezer to reduce the temperature by 1° C. per minute, until a temperature of –60° C. was reached. The vials were then transferred to liquid nitrogen storage tanks, where they may be maintained until needed.

The HRT-18G cells were reconstituted after removal from liquid nitrogen by rapid thawing (e.g., a total thawing period of about three minutes). The cells were then removed from their vial, seeded into 5 ml of growth medium into cell culture flasks, and incubated at 37° C. in an atmosphere containing 5% $CO_2$. The cells were allowed to attach to the bottom flask wall overnight. The medium was then removed and replaced with fresh medium. Growth of the cells then proceeded as described above.

A sample of the HRT-18G cell line was deposited with the American Type Culture Collection (ATCC), 12301 Parklawn Drive, Rockville, Md. 20852 on Jun. 15, 1994, and was assigned ATCC Accession No. nnnnn. This deposit was made pursuant to a contract between ATCC and the assignee of this patent application, Board of Supervisors of Louisiana State University and Agricultural and Mechanical College. The contract with ATCC provides for permanent and unrestricted availability of the HRT-18G cell line to the public on the issuance of the U.S. patent describing and identifying the deposit or the publication or the laying open to the public of any U.S. or foreign patent application, whichever comes first, and for availability of the progeny of the HRT-18G cell line to one determined by the U.S. Commissioner of Patents and Trademarks to be entitled thereto under pertinent statutes and regulations. The assignee of the present application has agreed that if the HRT-18G cell line on deposit should die or be lost or destroyed when cultivated under suitable conditions, it will be promptly replaced on notification with a viable culture of the same HRT-18G cell line.

Propagating Bovine Coronaviruses in Cell Line HRT-18G

Aside from its usefulness in diagnosing coronavirus as a factor in bovine shipping fever, the HRT-18G cell line is a substantially better host cell line than is the "parent" HRT-18 cell line for propagating known BECV's.

HRT-18 cells were grown either in DMEM prepared with distilled, heat sterilized water, or in Rosewell Park Memorial Institute medium 1640 ("RPMI-1640"). HRT-18G cells were grown in doubly deionized, filter-sterilized water.

The following BECV's were tested for replication in the cell cultures:

L9: a cell-culture adapted strain that had been previously propagated by serial passages in different cultured bovine cells in the presence of trypsin Vaccine: a cell-culture adapted strain, previously propagated in cultured bovine cells; related to L9

LY-138: a wild-type strain that does not replicate in cultured bovine cells

Meeker: a wild-type strain that does not replicate in cultured bovine cells

Fischer: a wild-type strain that does not replicate in cultured bovine cells

Calf 50: a wild-type strain that does not replicate in cultured bovine cells

Miller: a wild-type strain that does not replicate in cultured bovine cells

All BECV strains were inoculated into the host cells with 1 mg/ml trypsin in the growth medium. In the results given in the following table, "CPE" designates a cytopathic effect: –=negative, +=positive, F=fusion of cells. "HA" denotes hemagglutination of erythrocytes from mice (the units in these columns indicate the highest dilution—to the nearest factor of 2—at which a suspension of the viral culture would agglutinate a 0.5% suspension of mouse erythrocytes). "PFU"=plaque-forming units per ml of virus preparation. "ND"=not done.

| BECV | HRT-18 | | | HRT-18/RPMI-1640 | | | HRT-18G | | |
|---|---|---|---|---|---|---|---|---|---|
| Isolate | CPE | HA | PFU | CPE | HA | PFU | CPE | HA | PFU (× $10^7$) |
| L9 | — | <2 | ND | — | 16 | ND | +F | 128 | 8 |
| Vaccine | — | <2 | ND | — | 2 | ND | +F | 16 | 3.5 |
| LY-138 | — | <2 | ND | — | 2 | ND | +F | 64 | 6 |
| Meeker | — | <2 | ND | — | 2 | ND | +F | <4 | 9.5 |
| Fischer | — | <2 | ND | — | 2 | ND | +F | <8 | 8 |
| Miller | — | <2 | ND | — | ND | ND | +F | <2 | 3 |
| Calf 50 | — | <2 | ND | — | ND | ND | +F | <2 | 8 |

Isolation of Coronaviruses from Cattle with Shipping Fever

Clinical examinations were made and nasal samples were taken from 100 cattle between six and eight months of age having fever, nasal discharge, and respiratory distress on arrival in feedlots. These cattle did not exhibit symptoms of enteric disease. Fifty of these cattle originated from farms and ranches in Arkansas, Oklahoma, and Texas, were taken through sale yards, and were then transported to feedlots in Kansas. Another fifty of these cattle originated in California, and were transported to feedlots in Arizona. Nasal samples were collected from each side of the nose by brushing cotton-tipped swabs against the mucosal membranes. The swabs were placed in 4 ml of cell culture medium.

Duplicate samples were taken and tested in two different laboratories. In both laboratories, the same type of cytopathogenic coronaviruses were isolated from swabs of 38% of the cattle tested in HRT-18G cell cultures.

All viral strains were propagated in HRT-18G cells. Viruses were inoculated into HRT-18G cell cultures at a multiplicity of infection (MOI) of 0.1. After adsorption for one hour, the cells were washed with DPBS, fed with DMEM without serum, and incubated at 37° C. for 4 days.

Viral cultures were also attempted in GBK cells (Georgia bovine kidney cells) and BT cells (bovine turbinate cells), cell cultures that have conventionally been used in diagnosing previously known viral factors in shipping fever. BT and GBK cells are both known to be permissive for bovine herpesvirus 1 (BHV-1), and for parainfluenzavirus 3 (PI3). Bovine respiratory syncytial virus, BHV-1, PI3, and the cytopathogenic bovine viral diarrhea virus replicate in BT cells.

The newly-recognized coronavirus isolates replicated only in the HRT-18G cells, and did not replicate in either the BT or the GBK cells. Thus these coronaviruses would not have been detected through conventional diagnostic methods. Furthermore, these coronavirus isolates propagated in the HRT-18G cells did not induce cytopathic changes or hemagglutinin when inoculated into GBK and BT cells.

Twenty-two (22) different coronavirus isolates were established from 31 Oklahoma cattle, 6 isolates from 11 Texas cattle, and 4 isolates from 8 Arkansas cattle. Six isolates were obtained from the fifty California cattle. The cattle from which coronaviruses were recovered did not have multiple respiratory infections involving other bovine viruses; however samples from three cattle from Arizona that were negative for coronavirus isolates did yield PI3 virus in the BT cells. Control cell cultures remained normal with no viral infections. No other bovine viruses were propagated in the same laboratory while these 100 feedlot cattle samples were being tested.

It was a completely unexpected result that widespread coronavirus infections could be identified in cattle with clinical signs of shipping fever, when no other viruses were isolated or otherwise indicated as causing respiratory symptoms.

These viral isolates represent a unique bovine respiratory coronavirus that has been named bovine respiratory coronavirus-shipping fever ("BRCV-SF"). This identification is based on cytopathic interactions of BRCV-SF with the HRT-18G cells distinguishing the BRCV-SF viruses from bovine coronaviruses studied in the past. Distinguishing characteristics of the new BRCV-SF isolates include the following: (a) Isolation of BRCV-SF occurred in the first HRT-18G passage, without any trypsin enhancement. By contrast, trypsin activation has been needed in the past to isolate BECV's in the first passage on other cell culture lines, such as HRT-18 cells. (b) The BRCV-SF isolates had unusually high cell-fusing activity on the HRT-18G cells, meaning that they caused adjacent cells to "fuse" together into large, multinucleated entities at a high rate. (c) The BRCV-SF isolates, unlike vaccine strains that are used to immunize against BECV, had a restricted. hemagglutination pattern. The newly isolated BRCV-SF viruses agglutinated only mouse erythrocytes, and not chicken erythrocytes. By contrast, the Norden vaccine strain of BECV (currently in widespread use in the United States) agglutinates both mouse and chicken erythrocytes. (d) Unlike BECV strains, the BRCV-SF viruses did not form plaques in HRT-18G cells under conditions that facilitated plaque formation of the BECV strains tested.

Because the incidence of respiratory coronavirus infection was highest in the samples from Oklahoma cattle, a coronavirus isolate from one of the Oklahoma cattle, designated BRCV-OK-0514-2, was chosen as representative of the coronaviruses that have been implicated in shipping fever.

A sample of this BRCV-OK-0514-2 coronavirus isolate was deposited with the American Type Culture Collection (ATCC), 12301 Parklawn Drive, Rockville, Md. 20852 on Jun. 15, 1994, and was assigned ATCC Accession No. mmmmm. This deposit was made pursuant to a contract between ATCC and the assignee of this patent application, Board of Supervisors of Louisiana State University and Agricultural and Mechanical College. The contract with ATCC provides for permanent and unrestricted availability of the BRCV-OK-0514-2 coronavirus isolate to the public on the issuance of the U. S. patent describing and identifying the deposit or the publication or the laying open to the public of any U.S. or foreign patent application, whichever comes first, and for availability of the progeny of the BRCV-OK-0514-2 coronavirus isolate to one determined by the U.S. Commissioner of Patents and Trademarks to be entitled thereto under pertinent statutes and regulations. The assignee of the present application has agreed that if the BRCV-OK-0514-2 coronavirus isolate on deposit should become nonviable, or be lost or destroyed when cultivated under suitable conditions, it will be promptly replaced on notification with a viable sample of the same BRCV-OK-0514-2 coronavirus isolate.

The BRCV-OK-0514-2 coronavirus isolate may be used for comparison to other bovine respiratory coronavirus isolates, to determine in a particular case (through means known in the art) whether the same viral strain is responsible for an infection as is reported here. Also, the BRCV-OK-0514-2 coronavirus isolate may be propagated on the HRT-18G cell line, and the resulting viral particles may be purified from the cell culture as described below. The purified viral particles, or antigens or nucleotide sequences derived from those viral particles, will be used in preparing vaccines against the new coronavirus factor for shipping fever reported here.

Virus will be purified by the method of K. St. Cyr-Coats et al, "Structural Proteins of Bovine Coronavirus Strain L9: Effects of the Host Cell and Trypsin Treatment," Arch. Virol., vol. 103, pp. 35–45 (1988). Briefly, HRT-18G cells will be infected with BRCV-SF at an MOI of 0.01–0.1. Following adsorption for 1 hour at 37° C., excess inoculum will be removed, and cells will be washed three times with DPBS. DMEM will be added, and the cells will be incubated at 37° C. When a cytopathic effect has affected approximately 80% of the monolayer, the cells will be frozen at −70° C. After thawing, the infected material will be pooled into 250 ml centrifuge bottles, sonicated, and refrozen. The virus will be purified from the thawed cell lysate by isopycnic centrifugation in linear sucrose gradients. Gradient fractions will be collected by puncturing the bottom of the centrifuge tubes. Virus-containing fractions will be identified by hemagglutinating activity. Fractions containing the highest hemagglutinating activity will be pooled and concentrated by sedimentation through a 5 ml 20% sucrose cushion for 2 hours at 90,000×g. Virus will be resuspended in TNE buffer (0.01M tris-HCL, 0.01M NaCl, 0.001M EDTA, pH 7.4). This preparation is considered partially purified. For further purification, the virus suspension will be layered onto a preformed CsCl-TNE gradient (1.0606–1.2886 $g/cm^3$) and centrifuged at 55,000×g for 20 hours. Bands will be collected as described above, concentrated, and resuspended in TNE buffer.

The entire disclosures of all references cited in the specification are hereby incorporated by reference in their entirety. In the event of an otherwise irresolvable conflict, however, the present specification shall control.

I claim:

1. A cell from human rectal tumor cell line HRT-18G (ATCC accession number CRL 11663); or any progeny, mutant, or derivative of said ell line HRT-18G that possesses substantially the same susceptibility as cell line HRT-18G to bovine coronaviruses.

2. A cell culture comprising a plurality of cells as recited in claim 1.

3. A method of propagating bovine coronaviruses, comprising inoculating the coronaviruses into a cell culture as recited in claim 2.

4. A method as recited in claim 3, wherein bovine enteric coronaviruses are propagated.

5. A method as recited in claim 3, wherein bovine respiratory coronaviruses are propagated.

6. A method as recited in claim 5, wherein bovine respiratory coronaviruses taken from a bovine animal displaying symptoms of shipping fever are propagated.

7. A method of diagnosing a coronavirus as a factor in shipping fever in a bovine animal that has symptoms of shipping fever, comprising the steps of inoculating a sample from the animal's respiratory tract into a cell culture as recited in claim 2; and inspecting the cells for the presence of coronaviruses, or for the development of cytopathic changes.

8. A method of diagnosing a coronavirus as a factor in respiratory disease in a bovine animal that has symptoms of respiratory distress, wherein the animal does not have symptoms of intestinal distress, comprising the steps of inoculating a sample from the animal's respiratory tract into a cell culture as recited in claim 2; and inspecting the cells for the presence of coronaviruses, or for the development of cytopathic changes.

9. A composition of matter comprising purified viral particles of coronavirus isolate BRCV-OK-0514-2 (ATCC accession number VR 2460); or comprising purified viral particles of any progeny, mutant, or derivative of coronavirus isolate BRCV-OK-05314-2 that possesses substantially the same propensity to propagate in a culture of cell line HRT-18G (ATCC accession number CRL 11663).

10. A composition of matter as recited in claim 9, comprising purified viral particles of coronavirus isolate BRCV-OK-0514-2 (ATCC accession number VR 2460).

* * * * *